US012594225B2

(12) United States Patent (10) Patent No.: US 12,594,225 B2
Torii (45) Date of Patent: Apr. 7, 2026

(54) HAIR CLEANSING COMPOSITION

(71) Applicant: KAO CORPORATION, Tokyo (JP)

(72) Inventor: Shusaku Torii, Koto-ku (JP)

(73) Assignee: KAO CORPORATION, Tokyo (JP)

( * ) Notice: Subject to any disclaimer, the term of this patent is extended or adjusted under 35 U.S.C. 154(b) by 403 days.

(21) Appl. No.: 18/247,097

(22) PCT Filed: Sep. 29, 2021

(86) PCT No.: PCT/JP2021/035749
§ 371 (c)(1),
(2) Date: Mar. 29, 2023

(87) PCT Pub. No.: WO2022/071354
PCT Pub. Date: Apr. 7, 2022

(65) Prior Publication Data
US 2024/0016715 A1 Jan. 18, 2024

(30) Foreign Application Priority Data

Sep. 30, 2020 (JP) ................................. 2020-164647

(51) Int. Cl.
| | |
|---|---|
| *A61K 8/46* | (2006.01) |
| *A61K 8/73* | (2006.01) |
| *A61K 8/81* | (2006.01) |
| *A61Q 5/02* | (2006.01) |

(52) U.S. Cl.
CPC .............. *A61K 8/466* (2013.01); *A61K 8/731* (2013.01); *A61K 8/817* (2013.01); *A61Q 5/02* (2013.01); *A61K 2800/52* (2013.01)

(58) Field of Classification Search
CPC ........ A61K 8/466; A61K 8/731; A61K 8/817; A61K 2800/52; A61Q 5/02
See application file for complete search history.

(56) References Cited

U.S. PATENT DOCUMENTS

| | | | |
|---|---|---|---|
| 2015/0182438 A1* | 7/2015 | Fujii | A61K 8/737 |
| | | | 132/202 |
| 2015/0202133 A1 | 7/2015 | Doi et al. | |
| 2015/0239993 A1 | 8/2015 | Miyoshi et al. | |
| 2016/0122441 A1 | 5/2016 | Miyoshi et al. | |
| 2019/0183777 A1* | 6/2019 | Gillis | A61K 8/06 |
| 2021/0145720 A1 | 5/2021 | Morishima | |

FOREIGN PATENT DOCUMENTS

| | | | | | |
|---|---|---|---|---|---|
| AU | 2018327822 A1 | * | 2/2020 | ............... | C11D 1/37 |
| EP | 3527717 A1 | * | 8/2019 | .......... | D06M 13/288 |
| EP | 3 977 977 A1 | | 4/2022 | | |
| JP | 2014076988 A | * | 5/2014 | .......... | C11D 3/0094 |
| JP | 2014-131989 A | | 7/2014 | | |
| JP | 2015-25113 A | | 2/2015 | | |
| JP | 2015-27975 A | | 2/2015 | | |
| JP | 2015-27976 A | | 2/2015 | | |
| JP | 2023-54630 A | | 4/2023 | | |
| WO | WO 2019/022046 A1 | | 1/2019 | | |

OTHER PUBLICATIONS

International Search Report mailed on Nov. 22, 2021 in PCT/JP2021/035749 filed on Sep. 29, 2021, 2 pages).

* cited by examiner

*Primary Examiner* — Angela C Brown-Pettigrew
*Assistant Examiner* — Brittany Sharon Harris
(74) *Attorney, Agent, or Firm* — Oblon, McClelland, Maier & Neustadt, L.L.P.

(57) ABSTRACT

A hair cleansing composition including the following components (A) and (B): (A) an internal olefin sulfonic acid having 16 carbon atoms or a salt thereof, obtained by sulfonation of a raw material olefin having 16 carbon atoms and having an average double bond position of 3.9-position or more and 4.5-position or less, and (B) a cationic polymer. A mass ratio of a content of the component (A) to a content of the component (B), (A)/(B), is 1 or more and 500 or less.

15 Claims, No Drawings

HAIR CLEANSING COMPOSITION

CROSS REFERENCE TO RELATED APPLICATIONS

This application is a National Stage entry under 35 U.S.C. § 371 of PCT/JP2021/035749, filed on Sep. 29, 2021, and claims priority to Japanese Patent Application No. 2020-164647, filed on Sep. 30, 2020. The entire contents of both are incorporated herein by reference.

FIELD OF THE INVENTION

The present invention relates to a hair cleansing composition.

BACKGROUND OF THE INVENTION

Internal olefin sulfonates, which are known to have various numbers of carbon atoms, can achieve excellent effects as anionic surfactants and therefore have been conventionally used in various cleansing compositions.

For example, Patent Literature 1 discloses a cleansing composition containing an internal olefin sulfonate having 12 to 24 carbon atoms and a specific anionic surfactant not containing a sulfate group. It tries to provide good foam durability, quick rinsing, good combability, and so on, with being capable of containing other various surfactants. Furthermore, Patent Literature 2 discloses a skin or hair cleansing composition containing an internal olefin sulfonate similar to the above and a cationic polymer or amphoteric polymer. It tries to provide good feel, such as finger combability and moist feeling when applied to hair or skin, while enhancing the foam durability, rinsing property or the like, with being capable of containing other various surfactants.

Furthermore, Patent Literature 3 discloses a skin or hair cleansing composition containing a specific cationic-containing cellulose ether and another cationic polymer and being capable of containing an internal olefin sulfonate having 12 to 24 carbon atoms as an anionic surfactant, with enhancing finger combability and smoothness property when applied to hair or skin, the durability thereof, coated feeling or the like.

Patent Literature 1: JP-A-2015-27976
Patent Literature 2: JP-A-2015-27975
Patent Literature 3: JP-A-2014-131989

SUMMARY OF THE INVENTION

The present invention provides a hair cleansing composition containing the following components (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less; and (B) a cationic polymer, wherein the mass ratio of the content of the component (A) to the content of the component (B), (A)/(B), is 1 or more and 500 or less.

The internal olefin sulfonate can provide such various excellent performance to a composition, but enhances the hydrophobicity with an increase in the carbon chain length, resulting in increased melting point and hence ease of precipitation. Consequently, the low-temperature stability of the composition tends to decrease. However, in all the above Patent Literatures, there has been no consideration about giving good low-temperature stability, and there is still room for improvement.

Accordingly, the present inventor conducted various studies and found that a hair cleansing composition exhibiting excellent hair washing effect and exerting good low-temperature stability can be obtained by containing a specific internal olefin sulfonic acid or a salt thereof, obtained by sulfonation of a raw material olefin having an average double bond position within a limited range and cationic polymer.

That is, the present invention relates to a hair cleansing composition having excellent low-temperature stability, while enhancing the performance when applied to hair, by using a specific internal olefin sulfonic acid or a salt thereof.

The hair cleansing composition of the present invention when applied to hair provides good foaming and smooth foam quality at the time of washing, and softness of the hair can be realized at the time of rinsing. The composition also has excellent low-temperature stability and is a composition having high utility.

The "good foaming" at the time of washing hair by the hair cleansing composition of the present invention means quickly foaming sufficient volume of foam for washing and cleaning hair. The "smooth foam quality" at the time of washing hair by the hair cleansing composition of the present invention means clean and soft foam allowing to realize the protective effect spreading from the root to the tip of the hair. Furthermore, the "softness of hair" at the time of rinsing after washing of hair by the hair cleansing composition of the present invention means not only being capable of realizing softness and suppleness of the whole hair at the time of rinsing but also being capable of realizing flexibility and healthiness of each strand of hair at the time of finishing.

Hereinafter, these effects of "good foaming", "smooth foam quality", and "impartment of hair softness" when the hair cleansing composition of the present invention is applied to hair are also collectively referred to as "hair washing effect".

DETAILED DESCRIPTION OF THE INVENTION

The present invention will now be described in detail.

The hair cleansing composition of the present invention contains, as a component (A), an internal olefin sulfonic acid having 16 carbon atoms or a salt thereof, obtained by sulfonation of a raw material olefin having 16 carbon atoms and having an average double bond position of 3.9-position or more and 4.5-position or less. That is, the internal olefin sulfonic acid having 16 carbon atoms or a salt thereof as the component (A) is a compound that is obtained by using a raw material olefin having an average double bond position within a specific limited range as a starting raw material and sulfonating it. Specifically, it is the compound that is obtained by sulfonating a raw material olefin and then neutralizing and hydrolyzing it.

Examples of the salt of the internal olefin sulfonic acid having 16 carbon atoms obtained by sulfonation of a raw material olefin having 16 carbon atoms and having an average double bond position of 3.9-position or more and 4.5-position or less include one or more selected from the group consisting of alkali metal salts, such as a sodium salt and a potassium salt; organic amine salts, such as an ammonium salt, a monoethanolamine salt, a diethanolamine salt, a triethanolamine salt, a 2-aminoethanol salt, and a 2-aminomethyl propanediol salt; and basic amino acid salts, such as a lysine salt and an arginine salt. These internal olefin sulfonates having 16 carbon atoms may not be necessarily in a salt form from the beginning and may be a salt that is generated by a neutralization reaction during manufacturing.

In particular, the salt of the internal olefin sulfonic acid having 16 carbon atoms is, from the viewpoint of improving the low-temperature stability, preferably one or more selected from the group consisting of a sodium salt, a potassium salt, an ammonium salt, and a 2-aminoethanol salt, more preferably one or two selected from the group consisting of a sodium salt and a potassium salt, and further more preferably a sodium salt. That is, sodium internal olefin sulfonate having 16 carbon atoms is further more preferred.

The internal olefin sulfonic acid having 16 carbon atoms or a salt thereof as the component (A), which is a product obtained from such a raw material olefin having 16 carbon atoms, is mainly a mixture of hydroxyalkanesulfonic acid having 16 carbon atoms or a salt thereof (hydroxy form, abbreviation: "HAS") and olefin sulfonic acid having 16 carbon atoms or a salt thereof (olefin form, abbreviation: "IOS").

In the raw material olefin having 16 carbon atoms as a starting raw material of the component (A), the positions of double bonds are mainly located inside the carbon chain, but a so-called α-olefin in which the double bond is located at the 1-position of the carbon chain may be contained in a trace amount. When such a raw material olefin is sulfonated, β-sultone is mainly produced, and a part of the β-sultone is converted into γ-sultone and an olefin sulfonic acid. These β-sultone, γ-sultone, and olefin sulfonic acid are further converted into hydroxyalkanesulfonic acid having 16 carbon atoms or a salt thereof and olefin sulfonic acid having 16 carbon atoms or a salt thereof in the neutralization/hydrolysis process (for example, J. Am. Oil Chem. Soc. 69, 39 (1992)). The hydroxy group of the resulting hydroxyalkanesulfonic acid or a salt thereof is located inside the alkane chain, and the double bond of the olefin sulfonic acid or a salt thereof is located inside the olefin chain.

Accordingly, in the present specification, these products and a mixture thereof are collectively referred to as an internal olefin sulfonic acid having 16 carbon atoms or a salt thereof as the component (A).

The raw material olefin having 16 carbon atoms that is sulfonated and forms an internal olefin sulfonic acid having 16 carbon atoms or a salt thereof as the component (A) has an average double bond position of 3.9-position or more and 4.5-position or less. The raw material olefin having 16 carbon atoms and having an average double bond position of such a value has a broad distribution of double bond positions over from the 2-position to the 8-position including the 1-position that can be contained in a trace amount.

The double bond positions and its distribution in a raw material olefin can be verified by measurement using a gas chromatography mass spectrometer (abbreviation: "GC-MS"). Specifically, each of components having different carbon chain lengths and double bond positions is precisely separated by a gas chromatography apparatus (hereinafter, abbreviated as GC), and the double bond positions can be identified by application of them to a mass spectrometer (abbreviation: "MS"), and the distribution is determined from the respective GC peak areas.

On the other hand, in the internal olefin sulfonic acid having 16 carbon atoms or a salt thereof as the component (A) obtained by sulfonation of such a raw material olefin, the more the position of the sulfonate group introduced by sulfonation is inside the carbon chain, the more difficult the separation is. Accordingly, there is no definitive analytical method at present. However, the positions of the sulfonate groups in the component (A) are fully presumed to approximately correspond to the double bond positions in the raw material olefin and to show a broad distribution over from the 2-position to the 8-position including the 1-position without being excessively unevenly distributed. Accordingly, in the present invention, the component (A) is regulated based on the value of the average double bond position in the raw material olefin as a starting raw material.

The component (A) used in the present invention is an internal olefin sulfonic acid or a salt thereof obtained from a raw material olefin having the above-mentioned average double bond position value, i.e., a broad double bond distribution, and the sulfonate groups in the carbon chain are present in broad positions without being excessively unevenly distributed. In an internal olefin sulfonic acid having 16 carbon atoms or a salt thereof, if sulfonate groups are unevenly distributed near the end of the carbon chain, the melting point rises by an increase of the lengthened carbon chains, and precipitation easily occurs. Accordingly, the low-temperature stability may be deteriorated. In contrast, if sulfonate groups are unevenly distributed near the interior of the carbon chain, the foam quality at the time of washing and the feel of hair at the time of rinsing are deteriorated, and the hair washing effect may be reduced. However, in the internal olefin sulfonic acid having 16 carbon atoms or a salt thereof as the component (A) obtained from the above-mentioned raw material olefin, sulfonate groups are present in broad positions without being excessively unevenly distributed in the carbon chain, the internal olefin sulfonic acids or salts thereof having various lengths of the carbon chain from the bonding position of the sulfonate group to the end are moderately mixed. Accordingly, it is possible to exert good low-temperature storage stability, while maintaining the excellent hair washing effect, by using the component (A) in combination with component (B) described later. The same applies also when the component (A) is sodium internal olefin sulfonate having 16 carbon atoms.

The average double bond position (unit: position) in the raw material olefin having 16 carbon atoms as the starting raw material of the component (A) means the average value of the double bond positions of each raw material olefin having 16 carbon atoms present in the total amount of the raw material olefin having 16 carbon atoms. Specifically, the average double bond position of a raw material olefin having 16 carbon atoms is a value determined by the following formula (1).

$$\text{Average double bond position of raw material olefin having 16 carbon atoms} = \sum_{n=1}^{8} n \times C_n/100 \qquad (1)$$

(In the formula (1), n represents an integer (unit: position) indicating the position of a double bond existing in a raw material olefin having 16 carbon atoms; and $C_n$ represents the content (unit: mass %) of the raw material olefin having 16 carbon atoms and having a double bond at n-position in the total amount of 100 mass % of the raw material olefin having 16 carbon atoms.)

The average double bond position in the raw material olefin having 16 carbon atoms forming the component (A) is, from the viewpoint of securing the exertion of good low-temperature storage stability, 3.9-position or more, preferably 4.0-position or more, and more preferably 4.1-position or more. The average double bond position in the raw material olefin having 16 carbon atoms is, from the viewpoint of securing the exhibition of excellent hair washing effect, 4.5-position or less, preferably 4.4-position or less, and more preferably 4.2-position or less. In addition, the average double bond position in the raw material olefin having 16 carbon atoms is 3.9-position or more and 4.5-position or less, preferably from 4.0-position to 4.4-position, more preferably from 4.0-position to 4.2-position, and further more preferably from 4.1-position to 4.2-position.

In the raw material olefin having 16 carbon atoms, the content of a raw material olefin having a double bond position at the 2-position in the raw material olefin having 16 carbon atoms is preferably 10 mass % or more, more preferably 15 mass % or more, and further more preferably 20 mass % or more and preferably 35 mass % or less, more preferably 32 mass % or less, and further more preferably 24 mass % or less. In addition, in the raw material olefin having 16 carbon atoms, the content of the raw material olefin having a double bond position at the 2-position in the raw material olefin having 16 carbon atoms is preferably from 10 to 35 mass %, more preferably from 15 to 32 mass %, and further more preferably from 20 to 24 mass %.

In the raw material olefin having 16 carbon atoms, the content of a raw material olefin having a double bond position at the 3-position in the raw material olefin having 16 carbon atoms is preferably 10 mass % or more, more preferably 15 mass % or more, and further more preferably 20 mass % or more and preferably 30 mass % or less, more preferably 24 mass % or less, and further more preferably 19 mass % or less. In addition, in the raw material olefin having 16 carbon atoms, the content of the raw material olefin having a double bond position at the 3-position in the raw material olefin having 16 carbon atoms is preferably from 10 to 30 mass %, more preferably from 14 to 24 mass %, and further more preferably from 16 to 19 mass %.

In the raw material olefin having 16 carbon atoms, the content of a raw material olefin having a double bond position at the 4-position in the raw material olefin having 16 carbon atoms is preferably 10 mass % or more, more preferably 15 mass % or more, and further more preferably 17 mass % or more and preferably 30 mass % or less, more preferably 25 mass % or less, and further more preferably 19 mass % or less. In addition, in the raw material olefin having 16 carbon atoms, the content of the raw material olefin having a double bond position at the 4-position in the raw material olefin having 16 carbon atoms is preferably from 10 to 30 mass %, more preferably from 15 to 25 mass %, and further more preferably from 17 to 19 mass %.

In the raw material olefin having 16 carbon atoms, the content of a raw material olefin having a double bond position at the 5-position in the raw material olefin having 16 carbon atoms is preferably 5 mass % or more, more preferably 10 mass % or more, and further more preferably 13 mass % or more and preferably 25 mass % or less, more preferably 19 mass % or less, and further more preferably 15 mass % or less. In addition, in the raw material olefin having 16 carbon atoms, the content of the raw material olefin having a double bond position at the 5-position is preferably from 5 to 25 mass %, more preferably from 10 to 19 mass %, and further more preferably from 13 to 15 mass % in the raw material olefin having 16 carbon atoms.

In the raw material olefin having 16 carbon atoms, the content of a raw material olefin having a double bond position at the 6-position in the raw material olefin having 16 carbon atoms is preferably 5 mass % or more, more preferably 7 mass % or more, and further more preferably 11 mass % or more and preferably 20 mass % or less, more preferably 15 mass % or less, and further more preferably 13 mass % or less. In addition, in the raw material olefin having 16 carbon atoms, the content of the raw material olefin having a double bond position at the 6-position in the raw material olefin having 16 carbon atoms is preferably from 5 to 20 mass %, more preferably from 7 to 15 mass %, and further more preferably from 11 to 13 mass %.

In the raw material olefin having 16 carbon atoms, the total content of raw material olefins having a double bond position at the 7-position or 8-position in the raw material olefin having 16 carbon atoms is preferably 5 mass % or more, more preferably 7 mass % or more, and further more preferably 12 mass % or more and preferably 25 mass % or less, more preferably 22 mass % or less, and further more preferably 16 mass % or less. In addition, in the raw material olefin having 16 carbon atoms, the total content of the raw material olefins having a double bond position at the 7-position or 8-position in the raw material olefin having 16 carbon atoms is preferably from 5 to 25 mass %, more preferably from 7 to 22 mass %, and further more preferably from 12 to 16 mass %.

In the raw material olefin having 16 carbon atoms, the mass ratio of the content of raw material olefins having a double bond position at the 3- to 5-positions to the content of raw material olefins having a double bond position at the 6- to 8-positions, (raw material olefin 3 to 5-position/raw material olefin 6- to 8-position), is preferably 1.0 or more, more preferably 1.3 or more, and further more preferably 1.7 or more and preferably 4.0 or less, more preferably 3.5 or less, and further more preferably 2.2 or less. In addition, in the raw material olefin having 16 carbon atoms, the mass ratio of the content of raw material olefins having a double bond position at the 3- to 5-positions to the content of raw material olefins having a double bond position at the 6 to 8-positions, (raw material olefin 3 to 5-position/raw material olefin 6 to 8-position), is preferably from 1.0 to 4.0, more preferably from 1.3 to 3.5, and further more preferably from 1.7 to 2.2.

In the raw material olefin having 16 carbon atoms, the content of a raw material olefin having a double bond position at the 1-position ($\alpha$-olefin), which may inevitably exist, is preferably less than 5.0 mass %, more preferably less than 3.0 mass %, and further more preferably less than 2.5 mass % in the raw material olefin having 16 carbon atoms. Alternatively, the raw material olefin having 16 carbon atoms preferably does not contain $\alpha$-olefin.

The above-mentioned raw material olefin having 16 carbon atoms can be obtained by isomerization (double bond transfer) of a raw material olefin having a double bond position at the 1-position ($\alpha$-olefin) that is generated by dehydration reaction of an alcohol having 16 carbon atoms. Specifically, a solid acid catalyst, such as alumina, in an amount of preferably 0.5 parts by mass or more, more preferably 2 parts by mass or more, and preferably 15 parts by mass or less, more preferably 10 parts by mass or less, and preferably from 0.5 to 15 parts by mass, more preferably from 2 to 10 parts by mass, is added to 100 parts by mass of 1-hexadecanol.

Subsequently, isomerization reaction is performed by stirring at preferably 220° C. or more, more preferably 260° C. or more, and preferably 350° C. or less, and preferably from 220° C. to 350° C., more preferably from 260° C. to 350° C., for preferably 1 hour or more, more preferably 3 hours or more, and preferably 30 hours or less, more preferably 10 hours or less, and preferably from 1 to 30 hours, more preferably from 3 to 10 hours. The product after completion of the reaction is appropriately distilled to obtain above-mentioned raw material olefin having 16 carbon atoms.

In an internal olefin sulfonic acid having 16 carbon atoms or a salt thereof as the component (A) obtained by sulfonation of the above-described raw material olefin having 16 carbon atoms, the content of the internal olefin sulfonic acid having a sulfonate group at the 1-position or more and the 4-position or less or a salt thereof in the component (A) is preferably 40 mass % or more, more preferably 50 mass % or more, and further more preferably 55 mass % or more and preferably 75 mass % or less, more preferably 70 mass % or less, and further more preferably 68 mass % or less. In addition, in the internal olefin sulfonic acid having 16 carbon atoms or a salt thereof as the component (A) obtained by sulfonation of the above-described raw material olefin having 16 carbon atoms, the content of the internal olefin sulfonic acid having a sulfonate group at the 1-position or more and the 4-position or less or a salt thereof in the component (A) is preferably 40 mass % or more and 75 mass % or less, more preferably from 50 to 70 mass %, and further more preferably from 55 to 68 mass %.

When the component (A) is sodium internal olefin sulfonate having 16 carbon atoms, the content of sodium internal olefin sulfonate having a sulfonate group at the 1-position or more and 4-position or less in the sodium internal olefin sulfonate having 16 carbon atoms is also same as above.

In the internal olefin sulfonic acid having 16 carbon atoms or a salt thereof as the component (A), the content of an internal olefin sulfonic acid having a sulfonate group at the 2-position or a salt thereof in the component (A) is preferably 10 mass % or more, more preferably 13 mass % or more, and further more preferably 17 mass % or more and preferably 35 mass % or less, more preferably 30 mass % or less, and further more preferably 25 mass % or less. In addition, in the internal olefin sulfonic acid having 16 carbon atoms or a salt thereof as the component (A), the content of the internal olefin sulfonic acid having a sulfonate group at the 2-position or a salt thereof in the component (A) is preferably 10 mass % or more and 35 mass % or less, more preferably from 13 to 30 mass %, and further more preferably from 17 to 25 mass %.

When the component (A) is sodium internal olefin sulfonate having 16 carbon atoms, in the sodium internal olefin sulfonate having 16 carbon atoms, the content of sodium internal olefin sulfonate having a sulfonate group at the 2-position is also same as above.

In the internal olefin sulfonic acid having 16 carbon atoms or a salt thereof as the component (A), the content of an internal olefin sulfonic acid having a sulfonate group at the 3-position or a salt thereof in the component (A) is preferably 5 mass % or more, more preferably 11 mass % or more, and further more preferably 15 mass % or more and preferably 30 mass % or less, more preferably 25 mass % or less, and further more preferably 20 mass % or less. In addition, in the internal olefin sulfonic acid having 16 carbon atoms or a salt thereof as the component (A), the content of the internal olefin sulfonic acid having a sulfonate group at the 3-position or a salt thereof in the component (A) is preferably 5 mass % or more and 30 mass %, more preferably from 11 to 25 mass %, and further more preferably from 15 to 20 mass %.

When the component (A) is sodium internal olefin sulfonate having 16 carbon atoms, the content of sodium internal olefin sulfonate having a sulfonate group at the 3-position in the sodium internal olefin sulfonate having 16 carbon atoms is also same as above.

In the internal olefin sulfonic acid having 16 carbon atoms or a salt thereof as the component (A), the content of an internal olefin sulfonic acid having a sulfonate group at the 4-position or a salt thereof in the component (A) is preferably 15 mass % or more, more preferably 18 mass % or more, and further more preferably 19 mass % or more and preferably 30 mass % or less, more preferably 25 mass % or less, and further more preferably 23 mass % or less. In addition, in the internal olefin sulfonic acid having 16 carbon atoms or a salt thereof as the component (A), the content of the internal olefin sulfonic acid having a sulfonate group at the 4-position or a salt thereof in the component (A) is preferably 15 mass % or more and 30 mass % or less, more preferably from 18 to 25 mass %, and further more preferably from 19 to 23 mass %.

When the component (A) is sodium internal olefin sulfonate having 16 carbon atoms, in the sodium internal olefin sulfonate having 16 carbon atoms, the content of sodium internal olefin sulfate having a sulfonate group at the 4-position is also same as above.

In the internal olefin sulfonic acid having 16 carbon atoms or a salt thereof as the component (A), the content of an internal olefin sulfonic acid having a sulfonate group at the 1-position or a salt thereof in the component (A) is preferably less than 5.0 mass %, more preferably less than 3.0 mass %, and further more preferably less than 2.5 mass %. Alternatively, the internal olefin sulfonic acid having 16 carbon atoms or a salt thereof as the component (A) preferably does not contain the internal olefin sulfonic acid having a sulfonate group at the 1-position or a salt thereof.

When the component (A) is sodium internal olefin sulfonate having 16 carbon atoms, the content of sodium internal olefin sulfonate having a sulfonate group at the 1-position in the sodium internal olefin sulfonate having 16 carbon atoms is also same as above. Alternatively, it is preferable that the sodium internal olefin sulfonate having a sulfonate group at the 1-position is not contained.

In the internal olefin sulfonic acid having 16 carbon atoms or a salt thereof as the component (A), the mass ratio of the content of the hydroxy form (HAS) to the content of the olefin form (IOS), hydroxy form/olefin form, is preferably from 50/50 to 100/0, more preferably from 60/40 to 100/0, further more preferably from 70/30 to 100/0, further more preferably from 75/25 to 100/0, and more preferably from 75/25 to 95/5 from the viewpoint of productivity improvement and impurity reduction.

Such a mass ratio (hydroxy form/olefin form) is determined based on HPLC-MS peak areas that are obtained by separation of the hydroxy form and the olefin form from the component (A) by HPLC and application to MS.

When the component (A) is sodium internal olefin sulfonate having 16 carbon atoms, the mass ratio of the content of the hydroxy form (HAS) to the content of the olefin form (IOS), hydroxy form/olefin form, in the sodium internal olefin sulfonate having 16 carbon atoms is also same as above.

Since the internal olefin sulfonic acid having 16 carbon atoms or a salt thereof as the component (A) can be obtained by sulfonation of a raw material olefin, there is a possibility that the unreacted raw material olefin and the inorganic compound remain in the component (A). Lower contents of these components are preferable. The same applies also when the component (A) is sodium internal olefin sulfonate having 16 carbon atoms.

In the internal olefin sulfonic acid having 16 carbon atoms or a salt thereof as the component (A), the content of the unreacted raw material olefin in the component (A) is preferably less than 5.0 mass %, more preferably less than 3.0 mass %, further more preferably less than 1.5 mass %, and further more preferably less than 1.0 mass %.

When the component (A) is sodium internal olefin sulfonate having 16 carbon atoms, the content of the unreacted raw material olefin in the sodium internal olefin sulfonate having 16 carbon atoms is also same as above.

In the internal olefin sulfonic acid having 16 carbon atoms or a salt thereof as the component (A), the content of the inorganic compound in the component (A) is preferably less than 7.5 mass %, more preferably less than 5.0 mass %, further more preferably less than 3.0 mass %, further more preferably less than 2.0 mass %, and even more preferably less than 1.6 mass %.

When the component (A) is sodium internal olefin sulfonate having 16 carbon atoms, the content of the inorganic compound in the sodium internal olefin sulfonate having 16 carbon atoms is also same as above.

The content of the component (A) in a hair cleansing composition of the present invention is preferably 0.01 mass % or more, more preferably 0.05 mass % or more, further more preferably 0.1 mass % or more, further more preferably 1 mass % or more from the viewpoint of effectively promoting the exhibition of excellent hair washing effect. The content of the component (A) in the hair cleansing composition of the present invention is preferably 30 mass % or less, more preferably 15 mass % or less, further more preferably 12 mass % or less, further more preferably 10 mass % or less from the viewpoint of securing good low-temperature stability. In addition, the content of the component (A) in the hair cleansing composition of the present invention is preferably from 0.01 to 30 mass %, more preferably from 0.05 to 15 mass %, further more preferably from 0.1 to 12 mass %, further more preferably from 1 to 10 mass %.

The internal olefin sulfonic acid having 16 carbon atoms or a salt thereof as the component (A) can be obtained through sulfonation by reacting the raw material olefin having 16 carbon atoms with sulfur trioxide, specifically, by sulfonating the raw material olefin and then performing neutralization and subsequently hydrolysis.

More specifically, the amount of the sulfur trioxide that is used for sulfonation of the raw material olefin is preferably 0.8 mol or more, more preferably 0.9 mol or more, and further more preferably 0.95 mol or more based on 1 mol of the raw material olefin from the viewpoint of improving the yield of the component (A) and the viewpoint of improving the reactivity. In addition, the amount of the sulfur trioxide that is used for sulfonation of the raw material olefin is preferably 1.2 mol or less, more preferably 1.1 mol or less, and further more preferably 1.05 mol or less from the viewpoint of the economic efficiency and the viewpoint of suppressing unnecessary coloring of the component (A) In addition, the amount of the sulfur trioxide that is used for sulfonation of the raw material olefin is preferably from 0.8 to 1.2 mol, more preferably from 0.9 to 1.1 mol, and further more preferably from 0.95 to 1.05 mol based on 1 mol of the raw material olefin.

The reaction temperature when the raw material olefin is sulfonated is preferably 0° C. or more from the viewpoint of preventing coagulation of the sulfur trioxide and the component (A) and is preferably 50° C. or less from the viewpoint of suppressing unnecessary coloring of the component (A). The reaction temperature when the raw material olefin is sulfonated is preferably from 0° C. to 50° C.

In the neutralization, an alkali compound, such as sodium hydroxide, potassium hydroxide, ammonia, and 2-amino-ethanol, is used for the reaction. The amount of the alkali compound to be added is preferably 1.0 times mol or more, more preferably 1.03 times mol or more, per 1 mol of the sulfonate group from the viewpoint of suppressing the generation of impurities such as a raw material olefin and an inorganic salt and from the viewpoint of improving the reactivity. In addition, the amount of the alkali compound to be added is preferably 2.5 times mol or less, more preferably 2.0 times mol or less, and further more preferably 1.5 times mol or less per 1 mol of the sulfonate group from the viewpoint of the economic efficiency and the viewpoint of suppressing the generation of impurities such as a raw material olefin and an inorganic salt. The amount of the alkali compound to be added is preferably from 1.0 to 2.5 times mol, more preferably from 1.03 to 2.0 times mol, and further more preferably from 1.03 to 1.5 times mol per 1 mol of the sulfonate group.

In the neutralization, the temperature when the sulfonated raw material olefin and an alkali compound are mixed and the reaction temperature are preferably 40° C. or less, more preferably 35° C. or less, further more preferably 30° C. or less, and even more preferably 25° C. or less from the viewpoint of suppressing the generation of impurities, such as an internal olefin and an inorganic salt, by side reaction and is preferably 0° C. or more, more preferably 10° C. or more, further more preferably 15° C. or more, and even more preferably 20° C. or more from the viewpoint of improving the reactivity. In addition, the temperature when the sulfonated raw material olefin and an alkali compound are mixed and the reaction temperature are preferably from 0° C. to 40° C., more preferably from 10° C. to 35° C., further more preferably from 15° C. to 30° C., and even more preferably from 20° C. to 25° C.

The reaction temperature for hydrolysis that is performed after neutralization is preferably 120° C. or more, more preferably 140° C. or more, and further more preferably 160° C. or more from the viewpoint of improving the reactivity in the presence of water. In addition, the reaction temperature for the hydrolysis is preferably 220° C. or less and more preferably 180° C. or less from the viewpoint of suppressing decomposition of the product. In addition, the reaction temperature for the hydrolysis is preferably from 120° C. to 220° C., more preferably from 140° C. to 180° C., and further more preferably from 160° C. to 180° C.

The reaction time for the hydrolysis is preferably 30 minutes or more and more preferably 45 minutes or more from the viewpoint of completing the reaction. The reaction time for the hydrolysis is preferably 240 minutes or less, more preferably 180 minutes or less, further more preferably 120 minutes or less, and even more preferably 90 minutes or less from the viewpoint of improving the productivity. In addition, the reaction time for the hydrolysis is preferably from 30 to 240 minutes, more preferably from 45 to 180 minutes, further more preferably from 45 to 120 minutes, and even more preferably from 45 to 90 minutes. These reactions can be performed in series. After the completion of the reaction, purification can be performed by extraction, washing, and so on.

The hair cleansing composition of the present invention contains a cationic polymer as a component (B). Here, the term "cationic polymer" means a polymer having a substituent that is positively ionized when dissolved in water. By containing the component (B), it is possible to exhibit excellent hair washing effect and also secure good low-temperature stability due to the use of component (B) in combination with the component (A).

The same applies also when sodium internal olefin sulfonate having 16 carbon atoms is obtained as the component (A).

Specifically, examples of the component (B) include one or more selected from the group consisting of cationated polygalactomannan, cationated hydroxyalkyl cellulose, diallyl quaternary ammonium salt polymers, copolymers containing methacrylamidopropyltrimethylammonium chloride, and crosslinked cationic polymers.

More specifically, examples of the cationated polygalactomannan include one or more selected from the group consisting of cationated guar gum, cationated tara gum, cationated locust bean gum, and so on.

More specifically, examples of the cationated hydroxyalkyl cellulose include one or two selected from the group consisting of cationated hydroxyethyl cellulose, cationated hydroxypropyl cellulose, and so on.

More specifically, examples of the diallyl quaternary ammonium salt polymer include one or more selected from the group consisting of polydiallyldimethylammonium chloride, diallyldimethylammonium chloride/acrylic acid copolymers, diallyldimethylammonium chloride/acrylamide copolymers, and diallyldimethylammonium chloride/acrylic acid/acrylamide copolymers.

Examples of the copolymer containing methacrylamidopropyltrimethylammonium chloride include one or more selected from the group consisting of acrylic acid/methyl acrylate/methacrylamidopropyltrimethylammonium chloride copolymers and acrylic acid/acrylamide/methacrylamidopropyltrimethylammonium chloride copolymers.

More specifically, examples of the crosslinked cationic polymer include N,N-dimethylaminoethyl methacrylate diethyl sulfate/N,N-dimethylacrylamide/dimethacrylate polyethylene glycol copolymers.

In particular, from the viewpoint of achieving both the exhibition of excellent hair washing effect and the exertion of good low-temperature stability, one or more selected from the group consisting of cationated hydroxyalkyl cellulose and crosslinked cationic polymers are preferable, and cationated hydroxyethyl cellulose is further more preferable.

The content of the component (B) in the hair cleansing composition of the present invention is preferably 0.01 mass % or more, more preferably 0.05 mass % or more, further more preferably 0.1 mass % or more, and even more preferably 0.2 mass % or more from the viewpoint of effectively promoting the exhibition of excellent hair washing effect. The content of the component (B) in the hair cleansing composition of the present invention is preferably 10 mass % or less, more preferably 5 mass % or less, further more preferably 1 mass % or less, and even more preferably 0.8 mass % or less from the view point of securing good low-temperature stability. In addition, the content of the component (B) in the hair cleansing composition of the present invention is preferably 0.01 mass % or more and 10 mass % or less, more preferably from 0.05 to 5 mass %, further more preferably from 0.1 to 1 mass %, further more preferably from 0.2 to 1 mass %, and even more preferably from 0.2 to 0.8 mass %.

The mass ratio of the content of the component (A) to the content of the component (B), (A)/(B), is 1 or more, preferably 5 or more, more preferably 10 or more, and further more preferably 12 or more from the viewpoint of exhibiting good handling properties. The mass ratio of the content of the component (A) to the content of the component (B), (A)/(B), is 500 or less, preferably 100 or less, and more preferably 80 or less from the viewpoint of effectively providing also excellent hair washing effect. In addition, the mass ratio of the content of the component (A) to the content of the component (B), (A)/(B), is 1 or more and 500 or less, preferably from 5 to 100, more preferably from 10 to 80, and further more preferably from 12 to 80.

The hair cleansing composition of the present invention can contain an anionic surfactant (C) other than the component (A) from the viewpoint of further ensuring the exhibition of excellent hair washing effect and the exertion of good low-temperature stability due to the use of component (C) in combination with the component (A).

Specifically, examples of the component (C) include one or more selected from the group consisting of a sulfonate, an amino acid salt, a sulfosuccinate, a sulfuric ester salt, and a carboxylate.

The sulfonate as the component (C) is a sulfonate other than the component (A), and more specifically, examples of the sulfonate include one or more selected from the group consisting of aminoethyl sulfonates such as N-acylmethyltaurate, alkyl benzene sulfonates, alkenyl benzene sulfonates, alkane sulfonates, and α-olefin sulfonates having 14 carbon atoms.

More specifically, examples of the amino acid salt include one or more selected from the group consisting of acylglutamates, sarcosine derivatives, alanine derivatives, glycine derivatives, and arginine derivatives.

Examples of the sulfosuccinate include one or more selected from the group consisting of sulfosuccinic acid alkyl ester salts and polyoxyalkylene sulfosuccinic acid alkyl ester salts.

Examples of the sulfuric ester salt include one or more selected from the group consisting of alkyl sulfates, alkenyl sulfates, polyoxyalkylene alkyl ether sulfates, polyoxyalkylene alkenyl ether sulfates, polyoxyalkylene alkylphenyl ether sulfates and so on.

Examples of the carboxylate include one or more selected from the group consisting of fatty acid salts, polyoxyalkylene alkyl ether acetates, and so on.

In particular, from the viewpoint of achieving both the exhibition of excellent hair washing effect and the exertion of good low-temperature stability, one or more selected from the group consisting of aminoethyl sulfonate, amino acid salts, sulfosuccinates, polyoxyalkylene alkyl ether sulfates, and polyoxyalkylene alkyl ether acetates are preferable; one or more selected from the group consisting of aminoethyl sulfonate, amino acid salts, sulfosuccinates, and polyoxyalkylene alkyl ether sulfates are more preferable; and aminoethyl sulfonate is further preferable.

The content of the component (C) in the hair cleansing composition of the present invention is preferably 0.01 mass % or more, more preferably 0.05 mass % or more, further more preferably 0.1 mass % or more, and further more preferably 1 mass % or more from the viewpoint of effectively promoting the exhibition of excellent hair washing effect. The content of the component (C) in the hair cleansing composition of the present invention is preferably 30 mass % or less, more preferably 15 mass % or less, further more preferably 12 mass % or less, and further more preferably 9 mass % or less from the viewpoint of securing good low-temperature stability. In addition, the content of the component (C) in the hair cleansing composition of the present invention is preferably from 0.01 to 30 mass %, more preferably from 0.05 to 15 mass %, further more preferably from 0.1 to 12 mass %, and further more preferably from 1 to 9 mass %.

When the component (C) contains an internal olefin sulfonic acid or a salt thereof other than those having 16 carbon atoms, from the viewpoint of improving the smoothness of foam and low-temperature stability, the mass ratio of the content of the component (A) to the total amount of the internal olefin sulfonic acids or salts thereof in the hair cleansing composition of the present invention, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more.

The mass ratio of the content of the component (A) to the content of the component (C), (A)/(C), is preferably 0.01 or more, more preferably 0.05 or more, and further more preferably 0.1 or more from the viewpoint of effectively providing also excellent hair washing effect. The mass ratio of the content of the component (A) to the content of the component (C), (A)/(C), is preferably 100 or less, more preferably 25 or less, and further more preferably 15 or less from the viewpoint of effectively suppressing unnecessary precipitation of the component (A) and exhibiting good low-temperature stability. In addition, the mass ratio of the content of the component (A) to the content of the component (C), (A)/(C), is preferably from 0.01 to 100, more preferably from 0.05 to 25, and further more preferably from 0.1 to 15.

The hair cleansing composition of the present invention can contain an amphoteric surfactant (D) from the viewpoint of further ensuring the exhibition of excellent hair washing effect and the exertion of good low-temperature stability, by using the component (D) in combination with the component (A).

Specifically, examples of the component (D) include one or more selected from the group consisting of carbobetaines and sulfobetaines. More specifically, the examples include one or more selected from the group consisting of carbobetaines and sulfobetaines each including an alkyl group, alkenyl group, or acyl group having from 6 to 22 carbon atoms, preferably from 8 to 18 carbon atoms.

In particular, one or more selected from the group consisting of lauramidopropyl betaine, cocamidopropyl betaine, lauramidopropyl hydroxysulfobetaine, and lauryl sulfobetaine are preferable, and one or two selected from the group consisting of lauramidopropyl betaine and lauramidopropyl hydroxysulfobetaine are more preferable.

The content of the component (D) in the hair cleansing composition of the present invention is preferably 0.01 mass % or more, more preferably 0.05 mass % or more, and further more preferably 0.1 mass % or more from the viewpoint of further enhancing the exhibition of excellent hair washing effect. The content of the component (D) in the hair cleansing composition of the present invention is preferably 30 mass % or less, more preferably 15 mass % or less, and further more preferably 12 mass % or less from the viewpoint further certainly ensuring good low-temperature stability. In addition, the content of the component (D) in the hair cleansing composition of the present invention is preferably from 0.01 to 30 mass %, more preferably from 0.05 to 15 mass %, further more preferably from 0.1 to 12 mass %.

The mass ratio of the content of the component (A) to the content of the component (D), (A)/(D), is preferably 0.01 or more, more preferably 0.05 or more, and further more preferably 0.1 or more from the viewpoint of effectively suppressing unnecessary precipitation of the component (A) and exhibiting good low-temperature stability. The mass ratio of the content of the component (A) to the content of the component (D), (A)/(D), is preferably 50 or less, more preferably 25 or less, and further more preferably 9 or less from the viewpoint of effectively enhancing also excellent hair washing effect. In addition, the mass ratio of the content of the component (A) to the content of the component (D), (A)/(D), is preferably from 0.01 to 50, more preferably from 0.05 to 25, and further more preferably from 0.1 to 9.

The hair cleansing composition of the present invention can contain a nonionic surfactant (E) from the viewpoint of further ensuring the exhibition of excellent hair washing effect and the exertion of good low-temperature stability, due to the use of component (E) in combination with the above-mentioned components.

Specifically, examples of the component (E) include one or more selected from the group consisting of polyoxyalkylene alkyl ether, fatty acid alkanolamide, alkyl glycoside, and alkyl glyceryl ether.

More specifically, examples of the polyoxyalkylene alkyl ether include those of which the alkyl group has from 6 to 22 carbon atoms, preferably from 8 to 18 carbon atoms. In particular, polyoxyethylene alkyl ether is preferable, and those of which the oxyethylene group has an average number of moles added of from 3 to 50, more preferably from 4 to 16, are further preferable.

Examples of the fatty acid alkanolamide include mono- or di-alkanolamide of which the fatty acid has from 6 to 22 carbon atoms, preferably from 8 to 18 carbon atoms.

Examples of the alkyl glycoside include those of which the alkyl group has from 6 to 22 carbon atoms, preferably from 8 to 18 carbon atoms.

Examples of the alkyl glyceryl ether include those of which the alkyl group has from 6 to 22 carbon atoms, preferably from 8 to 18 carbon atoms.

In particular, fatty acid alkanolamide is more preferable.

The content of the component (E) in the hair cleansing composition of the present invention is preferably 0.01 mass % or more, more preferably 0.05 mass % or more, further more preferably 0.1 mass % or more, and further more preferably 0.5 mass % or more from the viewpoint of further enhancing the exhibition of excellent hair washing effect, by using the component (E) in combination with the component (B). The content of the component (E) in the hair cleansing composition of the present invention is preferably 15 mass % or less, more preferably 10 mass % or less, further more preferably 8 mass % or less, and further more preferably 6 mass % or less from the viewpoint of effectively ensuring good low-temperature stability, due to the use of component (E) in combination with the component (B). In addition, the content of the component (E) in the hair cleansing composition of the present invention is preferably from 0.01 to 15 mass %, more preferably from 0.05 to 10 mass %, further more preferably from 0.1 to 8 mass %, and further more preferably from 0.5 to 6 mass %.

The mass ratio of the content of the component (A) to the content of the component (E), (A)/(E), is preferably 0.01 or more, more preferably 0.05 or more, further more preferably 0.1 or more from the viewpoint of effectively suppressing unnecessary precipitation of the component (A) and exhibiting good low-temperature stability. The mass ratio of the content of the component (A) to the content of the component (E), (A)/(E), is preferably 50 or less, more preferably 25 or less, further more preferably 9 or less from the viewpoint of effectively providing also excellent hair washing effect. In addition, the mass ratio of the content of the component (A) to the content of the component (E), (A)/(E), is preferably from 0.01 to 50, more preferably from 0.05 to 25, further more preferably from 0.1 to 9.

The hair cleansing composition of the present invention can contain, in addition to the above-mentioned components, water that can be a medium when the component (A) is obtained by sulfonation of a raw material olefin, a viscosity reducer, polyhydric alcohols, a preservative, and a reducing agent, and also other components that are usually used as cosmetic raw materials, within ranges that do not impair the effects of the present invention. Examples of such components include a texture improver, a thickener, perfume, a UV absorber, a visible light absorber, a chelating agent, an antioxidant, a colorant, a preservative, a pH adjuster, a viscosity adjuster, a pearlescent agent, and a wetting agent.

The pH of the hair cleansing composition of the present invention at 25° C. is, as the pH of a 5% water dispersion, preferably 3.0 or more, more preferably 3.2 or more, and further more preferably 4.3 or more from the viewpoint of foaming at the time of washing. The pH of the hair cleansing composition of the present invention at 25° C. is, as the pH of a 5% water dispersion, preferably 7.0 or less, more preferably 6.5 or less, and further more preferably 6.0 or less from the viewpoint of suppressing entanglement of hair and so on. In addition, the pH of the hair cleansing composition of the present invention at 25° C. is, as the pH of a 5% water dispersion, preferably from 3.0 to 7.0, more preferably from 3.2 to 6.5, and further more preferably from 4.3 to 6.0.

The hair cleansing composition of the present invention usually contains an aqueous medium. Examples of the aqueous medium include water; lower alcohol, such as ethanol and isopropyl alcohol; and low molecular weight diol and triol having 6 or less carbon atoms, such as 1,3-butylene glycol, glycerin, ethylene glycol, and propylene glycol, and water is preferable. Although the content of the aqueous medium can be appropriately selected depending on the dosage form of the hair cleansing composition, the content in the hair cleansing composition is usually from 5 to 99 mass % and preferably from 30 to 98 mass %.

Thus, the hair cleansing composition of the present invention when applied to hair exerts performance of bringing about good foaming and also smooth foam quality at the time of washing and being capable of feeling hair softness at the time of rinsing, and the composition also has excellent low-temperature stability.

Accordingly, the use of the hair cleansing composition of the present invention is high in utility also as a hair washing method. Specifically, the hair washing method is, for example, a washing method in which the hair is moistened with water in advance, washed by applying the hair cleansing composition of the present invention to the hair, and then rinsed with water.

The use of the hair cleansing composition of the present invention is high in utility also as a low-temperature stabilization method for a hair cleansing composition.

Regarding the above-described embodiments, the present invention further discloses the following hair cleansing compositions:

[1] A hair cleansing composition comprising the following components (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less;

(B) a cationic polymer, wherein the mass ratio of the content of the component (A) to the content of the component (B), (A)/(B), is 1 or more and 500 or less;

[2] The hair cleansing composition according to the above [1], wherein the average double bond position of the raw material olefin having 16 carbon atoms that forms the component (A) is preferably 4.0-position or more and more preferably 4.1-position or more and preferably 4.4-position or less and more preferably 4.2-position or less;

[3] The hair cleansing composition according to the above [1] or [2], wherein in the raw material olefin having 16 carbon atoms, the content of the raw material olefin having a double bond position at the 2-position in the raw material olefin having 16 carbon atoms is preferably 10 mass % or more, more preferably 15 mass % or more, and further more preferably 20 mass % or more and preferably 35 mass % or less, more preferably 32 mass % or less, and further more preferably 24 mass % or less;

[4] The hair cleansing composition according to any one of the above [1] to [3], wherein in the raw material olefin having 16 carbon atoms, the content of the raw material olefin having a double bond position at the 3-position in the raw material olefin having 16 carbon atoms is preferably 10 mass % or more, more preferably 15 mass % or more, and further more preferably 20 mass % or more and preferably 30 mass % or less, more preferably 24 mass % or less, and further more preferably 19 mass % or less;

[5] The hair cleansing composition according to any one of the above [1] to [4], wherein in the raw material olefin having 16 carbon atoms, the content of the raw material olefin having a double bond position at the 4-position in the raw material olefin having 16 carbon atoms is preferably 10 mass % or more, more preferably 15 mass % or more, and further more preferably 17 mass % or more and preferably 30 mass % or less, more preferably 25 mass % or less, and further more preferably 19 mass % or less;

[6] The hair cleansing composition according to any one of the above [1] to [5], wherein in the raw material olefin having 16 carbon atoms, the content of the raw material olefin having a double bond position at the 5-position in the raw material olefin having 16 carbon atoms is preferably 5 mass % or more, more preferably 10 mass % or more, and further more preferably 13 mass % or more and preferably 25 mass % or less, more preferably 19 mass % or less, and further more preferably 15 mass % or less;

[7] The hair cleansing composition according to any one of the above [1] to [6], wherein in the raw material olefin having 16 carbon atoms, the content of the raw material olefin having a double bond position at the 6-position in the raw material olefin having 16 carbon atoms is preferably 5 mass % or more, more preferably 7 mass % or more, and further more preferably 11 mass % or more and preferably 20 mass % or less, more preferably 15 mass % or less, and further more preferably 13 mass % or less;

[8] The hair cleansing composition according to any one of the above [1] to [7], wherein in the raw material olefin having 16 carbon atoms, the total content of the raw material olefins having a double bond position at the 7-position or the 8-position in the raw material olefin having 16 carbon atoms is preferably 5 mass % or more, more preferably 7 mass % or more, and further more preferably 12 mass % or more and preferably 25 mass % or less, more preferably 22 mass % or less, and further more preferably 16 mass % or less;

[9] The hair cleansing composition according to any one of the above [1] to [8], wherein in the internal olefin sulfonic acid having 16 carbon atoms or a salt thereof as the component (A), the content of the internal olefin sulfonic acid having a sulfonate group at the 1-position or more and the 4-position or less or a salt thereof in the component (A) is preferably 40 mass % or more, more preferably 50 mass % or more, and further more preferably 55 mass % or more and preferably 75 mass % or less, more preferably 70 mass % or less, and further more preferably 68 mass % or less;

[10] The hair cleansing composition according to any one of the above [1] to [9], wherein in the internal olefin sulfonic acid having 16 carbon atoms or a salt thereof as the component (A), the content of the internal olefin sulfonic acid having a sulfonate group at the 2-position or a salt thereof in the component (A) is preferably 10 mass % or more, more preferably 13 mass % or more, and further more preferably 17 mass % or more and preferably 35 mass % or less, more preferably 30 mass % or less, and further more preferably 25 mass % or less;

[11] The hair cleansing composition according to any one of the above [1] to [10], wherein in the internal olefin sulfonic acid having 16 carbon atoms or a salt thereof as the component (A), the content of the internal olefin sulfonic acid having a sulfonate group at the 3-position or a salt thereof in the component (A) is preferably 5 mass % or more, more preferably 11 mass % or more, and further more preferably 15 mass % or more and preferably 30 mass % or less, more preferably 25 mass % or less, and further more preferably 20 mass % or less;

[12] The hair cleansing composition according to any one of the above [1] to [11], wherein in the internal olefin sulfonic acid having 16 carbon atoms or a salt thereof as the component (A), the mass ratio of the content of the hydroxy form (HAS) to the content of the olefin form (IOS), hydroxy form/olefin form, is preferably from 50/50 to 100/0, more preferably from 60/40 to 100/0, further more preferably from 70/30 to 100/0, further more preferably from 75/25 to 100/0, and more preferably from 75/25 to 95/5.

[13] The hair cleansing composition according to any one of the above [1] to [12], wherein the content of the component (A) is preferably 0.01 mass % or more, more preferably 0.05 mass % or more, further more preferably 0.1 mass % or more, further more preferably 1 mass % or more and preferably 30 mass % or less, more preferably 15 mass % or less, further more preferably 12 mass % or less, further more preferably 10 mass % or less;

[14] The hair cleansing composition according to any one of the above [1] to [13], wherein the component (B) is preferably one or more cationic polymers selected from the group consisting of cationated polygalactomannan, cationated hydroxyalkyl cellulose, diallyl quaternary ammonium salt polymers, and crosslinked cationic polymers, more preferably one or more selected from the group consisting of cationated hydroxyalkyl cellulose and crosslinked cationic polymers, and further more preferably cationated hydroxyethyl cellulose;

[15] The hair cleansing composition according to any one of the above [1] to [14], wherein the content of the component (B) is preferably 0.01 mass % or more, more preferably 0.05 mass % or more, further more preferably 0.1 mass % or more, further more preferably 0.2 mass % or more and preferably 10 mass % or less, more preferably 5 mass % or less, further more preferably 1 mass % or less, further more preferably 0.8 mass % or less;

[16] The hair cleansing composition according to any one of the above [1] to [15], wherein the mass ratio of the content of the component (A) to the content of the component (B), (A)/(B), is preferably 5 or more, more preferably 10 or more, further more preferably 12 or more and preferably 100 or less, more preferably 80 or less;

[17] The hair cleansing composition according to any one of the above [1] to [16], wherein the internal olefin sulfonic acid having 16 carbon atoms or a salt thereof as the component (A) is sodium internal olefin sulfonate having 16 carbon atoms;

[18] The hair cleansing composition according to any one of the above [1] to [17], wherein when an internal olefin sulfonic acid or a salt thereof other than those having 16 carbon atoms is included as a component (C), the mass ratio of the content of the component (A) to the total amount of the internal olefin sulfonic acids or salts thereof in the hair cleansing composition, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more;

[19] Use of a hair cleansing composition containing the following compositions (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less; and (B) a cationic polymer, wherein the mass ratio of the content of the component (A) to the content of the component (B), (A)/(B), is 1 or more and 500 or less;

[20] The use of a hair cleansing composition according to the above [19], wherein when an internal olefin sulfonic acid or a salt thereof other than those having 16 carbon atoms is included as a component (C), the mass ratio of the content of the component (A) to the total amount of the internal olefin sulfonic acids or salts thereof in the hair cleansing composition, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more;

[21] A hair washing method by applying a hair cleansing composition to hair, wherein the composition contains the following components (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less; and (B) a cationic polymer, wherein the mass ratio of the content of the component (A) to the content of the component (B), (A)/(B), is 1 or more and 500 or less.

[22] The hair washing method according to the above [21], wherein when an internal olefin sulfonic acid or a salt thereof other than those having 16 carbon atoms is included as a component (C), the mass ratio of the content of the component (A) to the total amount of the internal olefin sulfonic acids or salts thereof in the hair cleansing composition, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more.

[23] A low-temperature stabilization method for a hair cleansing composition by that the hair cleansing composition contains the following components (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less;

(B) a cationic polymer, wherein the mass ratio of the content of the component (A) to the content of the component (B), (A)/(B), is 1 or more and 500 or less.

[24] The low-temperature stabilization method for a hair cleansing composition according to the above [23], wherein when an internal olefin sulfonic acid or a salt thereof other than those having 16 carbon atoms is included as a component (C), the mass ratio of the content of the component (A) to the total amount of the internal olefin sulfonic acids or salts thereof in the hair cleansing composition, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more.

[25] Use of a hair cleansing composition for low-temperature stabilization, wherein the composition contains the following components (A) and (B):

(A) an internal olefin sulfonic acid having 16 carbon atoms or a salt thereof, obtained by sulfonation of a raw material olefin having 16 carbon atoms and having an average double bond position of 3.9-position or more and 4.5-position or less;

(B) a cationic polymer, wherein the mass ratio of the content of the component (A) to the content of the component (B), (A)/(B), is 1 or more and 500 or less.

[26] The use for low-temperature stabilization according to the above [25], wherein when an internal olefin sulfonic acid or a salt thereof other than those having 16 carbon atoms is included as a component (C), the mass ratio of the content of the component (A) to the total amount of the internal olefin sulfonic acids or salts thereof in the hair cleansing composition, (A)/(total amount of internal olefin sulfonic acids or salts thereof), is preferably 0.2 or more, preferably 0.4 or more, further more preferably 0.6 or more, even more preferably 0.8 or more, even more preferably 0.85 or more, even more preferably 0.9 or more, and even more preferably 0.95 or more.

Examples

The present invention will now be specifically described based on examples. Unless otherwise indicated in the table, the content of each component indicates mass %.

In addition, the measurement methods for various physical properties are as follows.

[Measurement Methods for Various Physical Properties]

(i) Method for Measuring Double Bond Position of Raw Material Olefin

The double bond position of a raw material olefin was measured by gas chromatography (hereinafter, abbreviated as GC). Specifically, a dithiolated derivative of a raw material olefin was obtained by reaction with dimethyl disulfide, and then each component was separated by GC. As a result, the double bond positions of the raw material olefin were determined from the respective peak areas.

The apparatuses and analysis conditions used for measurement are as follows: GC apparatus (trade name: HP6890, manufactured by Hewlett-Packard Company); column (trade name: Ultra-Alloy-1HT capillary column 30 m×250 m×0.15 μm, manufactured by Frontier Laboratories Ltd.); detector (hydrogen flame ionization detector (FID)); injection temperature: 300° C.; detector temperature: 350° C.; and He flow rate: 4.6 mL/min.

(ii) Method for Measuring Content According to Bonding Position of Sulfonate Group in Sodium Internal Olefin Sulfonate Regarding sodium internal olefin sulfonate with an attached sulfonate group, each sodium internal olefin sulfonate content according to the bonding position of sulfonate group was measured by high performance liquid chromatography/mass spectrometer (HPLC-MS). Specifically, hydroxy forms with a sulfonate group attached were separated by high performance liquid chromatography (HPLC) and were each applied to mass spectrometer (MS) for identification. As a result, each content was determined from the HPLC-MS peak areas.

The apparatuses and conditions used for measurement were as follows: HPLC apparatus "LD20ASXR" (manufactured by Shimadzu Corporation); column "ODS Hypersil (registered trademark)" (4.6×250 mm, particle size: 3 μm, manufactured by Thermo Fisher Scientific); sample preparation (1,000 times dilution with methanol); eluent A (10 mM ammonium acetate added water); eluent B (10 mM ammonium acetate added methacrylonitrile/water=95/5 (v/v) solution); gradient (0 minutes (A/B=60/40)→15.1 to 20 minutes (30/70)→20.1 to 30 minutes (60/40)); MS apparatus "LCMS-2020" (manufactured by Shimadzu Corporation); ESI detector (anion detection m/z: 321.10 ((A) component having 16 or 18 carbon atoms)); column temperature (40° C.); flow rate (0.5 mL/min); and injection volume (5 μL).

(iii) Method for Measuring Mass Ratio of Hydroxy Form/Olefin Form

The mass ratio of hydroxy form/olefin form of sodium internal olefin sulfonate was measured by HPLC-MS. Specifically, the hydroxy form and the olefin form were separated by HPLC and were respectively applied to MS for identification. As a result, the rate of each of them was determined from the HPLC-MS peak areas.

The apparatuses and conditions used for the measurement were as follows: HPLC apparatus (trade name: Agilent Technology 1100, manufactured by Agilent Technologies, Inc.); column (trade name: L-column ODS 4.6×150 mm, manufactured by Chemicals Evaluation and Research Institute, Japan); sample preparation (1,000 times dilution with methanol); eluent A (10 mM ammonium acetate added water); eluent B (10 mM ammonium acetate added methanol); gradient (0 minutes (A/B=30%/70%)→10 minutes (30%/70%)→55 minutes (0%/100%)→65 minutes (0%/100%)→66 minutes (30%/70%)→75 minutes (30%/70%)); MS apparatus (trade name: Agilent Technology 1100 MS SL (G1946D)); and MS detection (anion detection m/z 60-1600, UV 240 nm).

(iv) Method for Measuring Content of Raw Material Olefin

The content of unreacted raw material olefin in the sodium internal olefin sulfonate was measured by GC. Specifically, ethanol and petroleum ether were added to a sodium internal olefin sulfate aqueous solution, and extraction was then performed to obtain olefin in the petroleum ether phase. As a result, the raw material olefin was quantitatively measured from the GC peak area.

The apparatuses and analysis conditions used for the measurement were as follows: GC apparatus (trade name: Agilent Technology 6850, manufactured by Agilent Technologies, Inc.); column (trade name: Ultra-Alloy-1HT capillary column 15 m×250 μm×0.15 m, manufactured by Frontier Laboratories Ltd.); detector (hydrogen flame ionization detector (FID)); injection temperature: 300° C.; detector temperature: 350° C.; and He flow rate: 3.8 mL/min.

(v) Method for Measuring Content of Inorganic Compound

The contents of inorganic compounds were measured by potentiometric titration and neutralization titration.

Specifically, the content of $Na_2SO_4$ was quantitatively measured by determining the sulfate radical ($SO_4^{2-}$) by potentiometric titration. The content of NaOH was quantitatively measured by neutralization titration with dilute hydrochloric acid.

Production Example a1: Manufacturing of Raw Material Olefin a1 Having 16 Carbon Atoms 1-Hexadecanol (product name: KALCOL® 6098, manufactured by Kao Corporation) 7,000 g (28.9 mol) and γ-alumina (manufactured by STREM Chemicals, Inc.) 350 g (5 mass % with respect to the raw material alcohol) as a solid acid catalyst were placed in a flask equipped with a stirrer, and reaction was performed by stirring at 280° C. for 8 hours while circulating nitrogen (7,000 mL/min) in the system. The alcohol conversion rate after the completion of the reaction was 100%. The obtained crude alkene olefin was transferred to a distillation flask and was distilled at 136° C. to 160° C./4.0 mmHg to obtain a raw material olefin a1 having 16 carbon atoms with an olefin purity of 100%. The double bond distribution of the obtained raw material olefin a1 was C1-position: 1.8 mass %, C2-position: 21.8 mass %, C3-position: 18.7 mass %, C4-position: 18.6 mass %, C5-position: 14.3 mass %, C6-position: 11.4 mass %, and the total of C7- and C8-positions: 13.6 mass %, and the average double bond position was 4.17.

Production Example a2: Manufacturing of Raw Material Olefin a2 Having 16 Carbon Atoms A raw material olefin a2 having 16 carbon atoms was obtained with an olefin purity of 100% as in Production example a1 except that the reaction time was changed to 7.5 hours. The double bond distribution of the obtained raw material olefin a2 was C1-position: 2.4 mass %, C2-position: 23.2 mass %, C3-position: 18.7 mass %, C4-position: 18.2 mass %, C5-position: 13.9 mass %, C6-position: 11.2 mass %, and the total of C7- and the 8-positions: 12.4 mass %, and the average double bond position was 4.08.

Production Example a3: Manufacturing of Raw Material Olefin a3 Having 16 Carbon Atoms A raw material olefin a3 having 16 carbon atoms was obtained with an olefin purity of 100% as in Production example a1 except that the reaction time was changed to 8.5 hours. The double bond distribution of the obtained raw material olefin a3 was C1-position: 2.3 mass %, C2-position: 20.7 mass %, C3-position: 16.8 mass %, C4-position: 17.5 mass %, C5-position: 14.7 mass %, C6-position: 12.9 mass %, and the total of C7- and 8-positions: 15.2 mass %, and the average double bond position was 4.28.

Production Example a4: Manufacturing of Raw Material Olefin a4 Having 16 Carbon Atoms A raw material olefin a4 having 16 carbon atoms was obtained with an olefin purity of 100% as in Production example a1 except that the reaction time was changed to 6 hours. The double bond distribution of the obtained raw material olefin a4 was C1-position: 2.4 mass %, C2-position: 31.8 mass %, C3-position: 23.7 mass %, C4-position: 16.9 mass %, C5-position: 10.3 mass %, C6-position: 7.1 mass %, and the total of C7- and 8-positions: 7.9 mass %, and the average double bond position was 3.58.

Production Example a5: Manufacturing of Raw Material Olefin a5 Having 16 Carbon Atoms A raw material olefin a5 having 16 carbon atoms was obtained with an olefin purity of 100% as in Production example a1 except that the reaction time was changed to 11 hours. The double bond distribution of the obtained raw material olefin a5 was C1-position: 0.4 mass %, C2-position: 15.4 mass %, C3-position: 13.8 mass %, C4-position: 15.3 mass %, C5-position: 18.5 mass %, C6-position: 15.0 mass %, and the total of C7- and 8-positions: 21.6 mass %, and the average double bond position was 4.78.

Production Example a6: Manufacturing of Raw Material Olefin a6 Having 18 Carbon Atoms 1-Octadecanol (product name: KALCOL® 8098, manufactured by Kao Corporation) 7,000 g (25.9 mol) and γ-alumina (manufactured by STREM Chemicals, Inc.) 700 g (10 mass % with respect to the raw material alcohol) as a solid acid catalyst were placed in a flask equipped with a stirrer, and reaction was performed by stirring at 280° C. for 11 hours while circulating nitrogen (7,000 mL/min) in the system. The alcohol conversion rate after the completion of the reaction was 100%. The obtained crude alkene internal olefin was transferred to a distillation flask and was distilled at 148° C. to 158° C./0.5 mmHg to obtain a raw material olefin a6 having 18 carbon atoms with an olefin purity of 100%. The double bond distribution of the obtained raw material olefin a6 was C1-position: 1.8 mass %, C2-position: 26.4 mass %, C3-position: 21.1 mass %, C4-position: 17.5 mass %, C5-position: 11.7 mass %, C6-position: 8.3 mass %, C7-position: 5.9 mass %, and the total of C8- and 9-positions: 7.4 mass %, and the average double bond position was 4.00.

Production Example 1: Manufacturing of Sodium Internal Olefin Sulfonate A1 Having 16 Carbon Atoms The raw material olefin a1 obtained in Production example a1 was put in a thin film sulfonation reactor having an outer jacket, and sulfonation reaction was performed using a sulfur trioxide gas under the condition of allowing cooling water of 10° C. to pass through the reactor outer jacket. The molar ratio of $SO_3$/internal olefin during the sulfonation reaction was set to 1.01. The obtained sulfonated product was mixed with an alkali aqueous solution prepared with sodium hydroxide (alkali agent) in an amount of 1.04 times mol per mol of the theoretical acid value, and neutralization was performed by a continuous method at 30° C. for 1 hour. The obtained neutralized product was heated in an autoclave at 170° C. for 1 hour for hydrolysis to obtain sodium internal olefin sulfonate A1 having 16 carbon atoms. The content of the raw material olefin contained in the obtained sodium internal olefin sulfonate A1 having 16 carbon atoms was 0.4 mass %, and the content of the inorganic compound was 0.39 mass %.

Production Example 2: Manufacturing of Sodium Internal Olefin Sulfonate A2 Having 16 Carbon Atoms Sodium internal olefin sulfonate A2 having 16 carbon atoms was obtained as in Production example 1 except that the raw material olefin a2 obtained in Production example a2 was used as the raw material olefin. The content of the raw material olefin contained in the obtained sodium internal olefin sulfonate A2 having 16 carbon atoms was 0.7 mass %, and the content of the inorganic compound was 0.49 mass %.

Production Example 3: Manufacturing of Sodium Internal Olefin Sulfonate A3 Having 16 Carbon Atoms Sodium internal olefin sulfonate A3 having 16 carbon atoms was obtained as in Production example 1 except that the raw material olefin a3 obtained in Production example a3 was used as the raw material olefin. The content of the raw material olefin contained in the obtained sodium internal olefin sulfonate A3 having 16 carbon atoms was 0.5 mass %, and the content of the inorganic compound was 0.54 mass %.

Production Example 4: Manufacturing of Sodium Internal Olefin Sulfonate A4 Having 16 Carbon Atoms Sodium internal olefin sulfonate A4 having 16 carbon atoms was obtained as in Production example 1 except that the raw material olefin a4 obtained in Production example a4 was used as the raw material olefin. The content of the raw material olefin contained in the obtained sodium internal olefin sulfonate A4 having 16 carbon atoms was 0.4 mass %, and the content of the inorganic compound was 0.42 mass %.

Production Example 5: Manufacturing of Sodium Internal Olefin Sulfonate A5 Having 16 Carbon Atoms Sodium internal olefin sulfonate A5 having 16 carbon atoms was obtained as in Production example 1 except that the raw material olefin a5 obtained in Production example a5 was used as the raw material olefin. The content of the raw material olefin contained in the obtained sodium internal olefin sulfonate A5 having 16 carbon atoms was 0.2 mass %, and the content of the inorganic compound was 0.43 mass %.

Production Example 6: Manufacturing of Sodium Internal Olefin Sulfonate A6 Having 18 Carbon Atoms Sodium internal olefin sulfonate A6 having 18 carbon atoms was obtained as in Production example 1 except that the raw material olefin a6 obtained in Production example a6 was used as the raw material olefin. The content of the raw material olefin contained in the obtained sodium internal olefin sulfonate A6 having 18 carbon atoms was 0.5 mass %, and the content of the inorganic compound was 0.45 mass %.

Each of the physical property values of the obtained raw material olefins a1 to a6 and sodium internal olefin sulfonates A1 to A6 are shown in Tables 1 to 2.

TABLE 1

| Raw material olefin | | a1 | a2 | a3 | a4 | a5 | a6 |
|---|---|---|---|---|---|---|---|
| Number of carbon atoms | | 16 | 16 | 16 | 16 | 16 | 18 |
| Double bond | C1-position | 1.8 | 2.4 | 2.3 | 2.4 | 0.4 | 1.8 |
| distribution in | C2-position | 21.8 | 23.2 | 20.7 | 31.8 | 15.4 | 26.4 |
| raw material | C3-position | 18.7 | 18.7 | 16.8 | 23.7 | 13.8 | 21.1 |
| olefin (mass %) | C4-position | 18.6 | 18.2 | 17.5 | 16.9 | 15.3 | 17.5 |
| | C5-position | 14.3 | 13.9 | 14.7 | 10.3 | 18.5 | 11.7 |
| | C6-position | 11.4 | 11.2 | 12.9 | 7.1 | 15.0 | 8.3 |
| | C7-position | 6.8 | 6.2 | 7.6 | 3.9 | 10.8 | 5.9 |
| | C8-position | 6.8 | 6.2 | 7.6 | 3.9 | 10.8 | 3.7 |
| | C9-position | | | | | | 3.7 |
| | Total | 100.0 | 100.0 | 100.0 | 100.0 | 100.0 | 100.0 |
| Average double bond position | | 4.17 | 4.08 | 4.28 | 3.58 | 4.78 | 4.00 |

TABLE 2

| Sodium internal olefin sulfonate | | A1 | A2 | A3 | A4 | A5 | A6 |
|---|---|---|---|---|---|---|---|
| Raw material olefin | | a1 | a2 | a3 | a4 | a5 | a6 |
| Distribu- | C1-position | 2.0 | 1.2 | 1.6 | 1.5 | 0.6 | 1.4 |
| tion of | C2-position | 24.8 | 18.7 | 17.5 | 16.7 | 13.1 | 20.7 |
| sulfonate | C3-position | 19.1 | 16.1 | 15.7 | 14.2 | 11.5 | 17.4 |
| group | C4-position | 22.0 | 19.9 | 20.3 | 18.5 | 18.0 | 21.0 |
| (mass %) | C5- to C9-positions | 32.1 | 44.2 | 45.0 | 49.1 | 56.8 | 39.6 |
| | Total | 100 | 100 | 100 | 100 | 100 | 100 |
| Hydroxy form | | 83.9 | 84.2 | 83.8 | 84.1 | 84.6 | 83.8 |
| Olefin form | | 16.1 | 15.8 | 16.2 | 15.9 | 15.4 | 16.2 |

Examples 1 to 16 and Comparative Examples 1 to 7

Hair cleansing compositions having the compositions shown in Tables 3 to 6 were prepared by a usual method using the obtained sodium internal olefin sulfonates A1 to A6 or sodium α-olefin sulfonate A7 having 14 carbon atoms (Lipolan® LB-400, manufactured by Lion Corporation). Specifically, a component (A), a component (B), an appropriate amount of water, and a component (C) as needed were placed in a beaker and were heated to 60° C., mixed, and cooled to room temperature. Subsequently, water was replenished, and the pH was adjusted to 5.6 with a pH adjuster (succinic acid or disodium succinate aqueous solution) to obtain each hair cleansing composition.

Each evaluation was performed using the obtained hair cleansing compositions according to the following methods.

The results are shown in Tables 3 to 6.

<<Evaluation of Hair Washing Effect>>

The components shown below were placed in a beaker and were heated to 80° C. and then mixed, and after confirmation of uniform dissolution, cooled to obtain plain shampoo.

(Composition of Plain Shampoo)

| (Component) | (mass %) |
|---|---|
| Na polyoxyethylene lauryl ether sulfate (42.0% as EMAL ® E-27C (manufactured by Kao Corporation, active component: 27 mass)) | 11.3 |
| Coconut fatty acid N-methylethanolamide (AMINON ® C-11S (manufactured by Kao Corporation)) | 3.0 |
| Citric acid | 0.2 |
| Methylparaben | 0.3 |
| Purified water | balance |
| Total | 100.0 |

A Japanese untreated hair bundle having a mass of 20 g and a length of 20 cm was washed with the plain shampoo to obtain a hair bundle for evaluation of foaming. The obtained hair bundle for evaluation was sufficiently wetted with warm water of 35° C. to 40° C., and 1 g of any of the hair cleansing compositions was then applied to the hair bundle, followed by washing for 1 minute. Each of the items of "good foaming" and "smooth foam quality" at the time of washing and "softness of hair" at the time of rinsing were evaluated by scores by five special panelists according to the following evaluation criteria, and the average values thereof were determined.

The average value "3" was used as a standard and used as an index for evaluation. When the average score of five panelists was 3 points or more, it was judged to be acceptable.

7: Very good,
6: Better,
5: Good,
4: Somewhat good,
3: Standard,
2: Bad, and
1: Very bad.

<<Evaluation of Low-Temperature Stability>>

The obtained hair cleansing compositions were put in respective screw bottles and were stored in a thermostat chamber of −5° C. Subsequently, whether precipitate was formed over time was visually checked and evaluated according to the following criteria:

a: Formation of precipitate was not observed even after the lapse of 6 hours;

b: Formation of precipitate was observed during the lapse of 5 hours or more and less than 6 hours; and c: Formation of precipitate was observed before the lapse of less than 5 hours.

TABLE 3

|  |  | Example |  |  |  |  | Comparative Example |  |
|---|---|---|---|---|---|---|---|---|
|  |  | 1 | 2 | 3 | 4 | 5 | 1 | 2 |
| (A) | Sodium C16 internal olefin sulfonate A1 | 10.00 | 10.00 | 10.00 | 10.00 | 10.00 | 10.00 |  |
| (B) | Cationated hydroxyethyl cellulose B1*[1] | 1.00 | 0.75 | 0.50 | 0.30 | 0.10 |  | 0.50 |
|  | Purified water | Balance | Balance | Balance | Balance | Balance | Balance | Balance |
|  | Total | 100.00 | 100.00 | 100.00 | 100.00 | 100.00 | 100.00 | 100.00 |
|  | (A)/(B) | 10.00 | 13.33 | 20.00 | 33.33 | 100.00 | — | — |
|  | Foaming | 3 | 4 | 5 | 5 | 3 | 3 | 1 |
|  | Smoothness of foam | 3 | 5 | 5 | 5 | 5 | 3 | 1 |
|  | Softness of hair | 5 | 5 | 5 | 5 | 3 | 3 | 1 |
|  | Low-temperature stability | a | a | a | a | b | c | a |

*[1]SoftCAT ™ Polymer SL-30 (Polyquaternium-67), manufactured by The Dow Chemical Company

TABLE 4

|  |  | Example |  |  | Comparative Example |  |  |  |
|---|---|---|---|---|---|---|---|---|
|  |  | 6 | 4 | 7 | 3 | 4 | 5 | 6 |
| (A) | Sodium C16 internal olefin sulfonate A2 | 10.00 |  |  |  |  |  |  |
|  | Sodium C16 internal olefin sulfonate A1 |  | 10.00 |  |  |  |  |  |
|  | Sodium C16 internal olefin sulfonate A3 |  |  | 10.00 |  |  |  |  |
|  | Sodium C16 internal olefin sulfonate A4 |  |  |  | 10.00 |  |  |  |
|  | Sodium C16 internal olefin sulfonate A5 |  |  |  |  | 10.00 |  |  |
|  | Sodium C18 internal olefin sulfonate A6 |  |  |  |  |  |  | 10.00 |
|  | Sodium C14 α-olefin sulfonate A7*[2] |  |  |  |  |  | 10.00 |  |
| (B) | Cationated hydroxyethyl cellulose B1*[1] | 0.30 | 0.30 | 0.30 | 0.30 | 0.30 | 0.30 | 0.30 |
|  | Purified water | Balance | Balance | Balance | Balance | Balance | Balance | Balance |
|  | Total | 100.00 | 100.00 | 100.00 | 100.00 | 100.00 | 100.00 | 100.00 |
|  | (A)/(B) | 33.33 | 33.33 | 33.33 | — | — | — | — |
|  | Foaming | 4 | 5 | 4 | 3 | 4 | 4 | 2 |
|  | Smoothness of foam | 5 | 5 | 5 | 4 | 5 | 2 | 3 |

TABLE 4-continued

|  | Example | | | Comparative Example | | | |
|---|---|---|---|---|---|---|---|
|  | 6 | 4 | 7 | 3 | 4 | 5 | 6 |
| Softness of hair | 5 | 5 | 4 | 4 | 2 | 3 | 4 |
| Low-temperature stability | a | a | a | c | a | a | c |

[1]Same as Table 3
[2]Lipolan ® LB-400, manufactured by Lion Corporation

TABLE 5

|  | Example | | | | | | | Comparative Example |
|---|---|---|---|---|---|---|---|---|
|  | 4 | 8 | 9 | 10 | 11 | 12 | 13 | 7 |
| (A) Sodium C16 internal olefin sulfonate A1 | 10.00 | 10.00 | 10.00 | 10.00 | 10.00 | 10.00 | 10.00 | 10.00 |
| (B) Cationated hydroxyethyl cellulose B1[1] | 0.30 |  |  |  |  |  |  |  |
| Cationated hydroxyethyl cellulose B2[3] |  | 0.30 |  |  |  |  |  |  |
| Crosslinked cationic polymer[4] |  |  | 0.30 |  |  |  |  |  |
| Cationated polygalactomannan[5] |  |  |  | 0.30 |  |  |  |  |
| Cationated hydroxyalkyl cellulose[6] |  |  |  |  | 0.30 |  |  |  |
| Copolymer containing methacrylamidopropyltrimethylammonium chloride[7] |  |  |  |  |  | 0.30 |  |  |
| Diallyl quaternary ammonium salt polymer[8] |  |  |  |  |  |  | 0.30 |  |
| Hydroxyethyl cellulose[9] |  |  |  |  |  |  |  | 0.30 |
| Purified water | Balance | Balance | Balance | Balance | Balance | Balance | Balance | Balance |
| Total | 100.00 | 100.00 | 100.00 | 100.00 | 100.00 | 100.00 | 100.00 | 100.00 |
| (A)/(B) | 33.33 | 33.33 | 33.33 | 33.33 | 33.33 | 33.33 | 33.33 | — |
| Foaming | 5 | 4 | 5 | 4 | 5 | 5 | 5 | 4 |
| Smoothness of foam | 5 | 5 | 5 | 5 | 5 | 5 | 5 | 4 |
| Softness of hair | 5 | 4 | 5 | 4 | 3 | 3 | 3 | 2 |
| Low-temperature stability | a | a | b | b | b | b | b | a |

[1]Same as Table 3
[3]UCARE ™ Polymer LR-400 (Polyquaternium-10), manufactured by The Dow Chemical Company
[4]SOFCARE ® KG-101W-E (Polyquaternium-52), manufactured by Kao Corporation
[5]Jaguar ® Excel, manufactured by Solvay S.A.
[6]SOFCARE ® C-HP2-W, manufactured by Kao Corporation
[7]Merquat ™ 2001, manufactured by The Lubrizol Corporation
[8]Merquat ™ 280NP, manufactured by The Lubrizol Corporation
[9]HEC Daicel ™ SE850K, manufactured by Daicel Corporation

TABLE 6

|  | Example | | |
|---|---|---|---|
|  | 14 | 15 | 16 |
| (A) Sodium C16 internal olefin sulfonate A1 | 7.00 | 7.00 | 7.00 |
| (B) Cationated hydroxyethyl cellulose B2[3] | 0.10 | 0.15 | 0.20 |
| Cationated hydroxyethyl cellulose B1[1] | 0.35 | 0.15 |  |
| (C) Sodium cocoyl methyl taurine[10] | 1.70 | 1.00 | 3.00 |
| (D) Lauramidopropyl hydroxysultaine[11] | 2.70 | 1.00 | 1.00 |
| Lauramidopropyl betaine[12] | 0.30 | 1.00 | 3.00 |
| (E) Polyoxyethylene (6) lauryl ether[13] | 1.00 | 0.25 | 0.50 |
| Cocoyl N-methylethanolamide[14] | 1.20 | 0.25 | 1.50 |
| Lauryl glucoside[15] | 1.70 | 0.50 | 0.25 |
| 2-Ethylhexylglyceryl ether[16] | 0.11 |  | 0.05 |
| Preservative | 0.10 | 0.10 | 0.10 |
| Solvent | 0.75 | 0.75 | 0.75 |
| pH adjuster | 0.20 | 0.20 | 0.20 |
| Purified water | Balance | Balance | Balance |
| Total | 100.00 | 100.00 | 100.00 |
| (A)/(B) | 15.56 | 23.33 | 35.00 |
| (A)/(C) | 4.12 | 7.00 | 2.33 |
| (A)/(D) | 2.33 | 3.50 | 1.75 |
| (A)/(E) | 1.75 | 7.00 | 3.04 |

TABLE 6-continued

|  | Example | | |
|---|---|---|---|
|  | 14 | 15 | 16 |
| Foaming | 7 | 7 | 7 |
| Smoothness of foam | 7 | 7 | 7 |
| Softness of hair | 7 | 7 | 7 |
| Low-temperature stability | a | a | a |

[1], [3]Same as Table 3
[10]DIAPON ® K-SF, manufactured by NOF Corporation
[11]SOFTAZOLINE ™ LSB-R, manufactured by Kawaken Fine Chemicals Co., Ltd.
[12]SOFTAZOLINE ™ LPB-R, manufactured by Kawaken Fine Chemicals Co., Ltd.
[13]EMULGEN ® 108, manufactured by Kao Corporation
[14]AMINON ® C-11S, manufactured by Kao Corporation
[15]AG-124, manufactured by Kao Corporation
[16]PENETOL ® GE-EH, manufactured by Kao Corporation

The invention claimed is:

1. A hair cleansing composition comprising following components (A) and (B):

(A) an internal olefin sulfonic acid having 16 carbon atoms or a salt thereof, obtained by sulfonation of a raw material olefin having 16 carbon atoms and having an average double bond position of 4.0-position to 4.4-position; and (B) cationated hydroxyethyl cellulose, wherein
a mass ratio of a content of the component (A) to a content
of the component (B), (A)/(B), is 12 or more and 80 or
less, and
in the raw material olefin having 16 carbon atoms,
a content of a raw material olefin having a double bond
position at a 1-positon is less than 5.0 mass %;
a content of a raw material olefin having a double bond
position at a 2-positon is from 20 to 24 mass %; and
a content of a raw material olefin having a double bond
position at a 7-position or 8-position is from 12 to 16
mass %, each based on a total mass of the raw
material olefin.

2. The hair cleansing composition according to claim 1,
wherein a content of an internal olefin sulfonic acid including a sulfonate group at a 1-position or more and a 4-position
or less or a salt thereof is 40 mass % or more and 75 mass
% or less in the component (A).

3. The hair cleansing composition according to claim 1,
wherein a content of an internal olefin sulfonic acid including a sulfonate group at a 2-position or a salt thereof is 10
mass % or more and 35 mass % or less in the component
(A).

4. The hair cleansing composition according to claim 1,
wherein a content of an internal olefin sulfonic acid including a sulfonate group at a 3-position or a salt thereof is 5
mass % or more and 30 mass % or less in the component
(A).

5. The hair cleansing composition according to claim 1,
wherein a content of the component (A) is 0.01 mass % or
more and 30 mass % or less, based on a total mass of the
composition.

6. The hair cleansing composition according to claim 1,
wherein a mass ratio of a content of a hydroxy form of the
internal olefin sulfonic acid or a salt thereof to a content of
an olefin form of the internal olefin sulfonic acid or a salt
thereof, (hydroxy form/olefin form), in the component (A) is
from 50/50 to 100/0.

7. The hair cleansing composition according to claim 1,
wherein a content of the component (B) is 0.01 mass % or
more and 10 mass % or less, based on a total mass of the
composition.

8. The hair cleansing composition according to claim 1,
wherein a content of the internal olefin sulfonic acid including a sulfonate group at a 4-position or a salt thereof is 15
mass % or more and 30 mass % or less in the component
(A).

9. The hair cleansing composition according to claim 1,
wherein the mass ratio of the content of the component (A)
to the content of the component (B), (A)/(B), is from 5 to
100.

10. The hair cleansing composition according to claim 1,
wherein a content of an internal olefin sulfonic acid including a sulfonate group at a 1-position or a salt thereof is less
than 3.0 mass % in the component (A).

11. The hair cleansing composition according to claim 1,
further comprises component (C) an internal olefin sulfonic
acid or a salt thereof other than component (A), wherein a
mass ratio of the content of the component (A) to a total
amount of the internal olefin sulfonic acids or salts thereof,
(A)/(total amount of internal olefin sulfonic acids or salts
thereof), is 0.95 or more.

12. A method of washing hair, comprising:
moistening the hair with water;
washing the hair by applying the hair cleansing composition according to claim 1 to the hair; and
rinsing the hair with water.

13. A low-temperature stabilization method for a hair
cleansing composition, the method comprising mixing the
following components (A) and (B) with water:
(A) an internal olefin sulfonic acid having 16 carbon
atoms or a salt thereof, obtained by sulfonation of a raw
material olefin having 16 carbon atoms and having an
average double bond position of 4.0-position to 4.4-
position; and
(B) cationated hydroxyethyl cellulose, wherein
a mass ratio of a content of the component (A) to a content
of the component (B), (A)/(B), is 12 or more and 80 or
less, and
in the raw material olefin having 16 carbon atoms,
a content of a raw material olefin having a double bond
position at a 1-positon is less than 5.0 mass %;
a content of a raw material olefin having a double bond
position at a 2-positon is from 20 to 24 mass %; and
a content of a raw material olefin having a double bond
position at a 7-position or 8-position is from 12 to 16
mass %, each based on a total mass of the raw
material olefin.

14. The hair cleansing composition according to claim 1,
wherein in the internal olefin sulfonic acid having 16 carbon
atoms or a salt thereof, a content of an internal olefin
sulfonic acid having a sulfonate group at a 1-position to a
4-position is 55% to 68% by mass, based on a total mas of
the internal olefin sulfonic acid having 16 carbon atoms or
a salt thereof.

15. The hair cleansing composition according to claim 1,
wherein in the raw material olefin having 16 carbon atoms,
a content of a raw material olefin having a double bond
position at a 3-positon is from 16 to 19 mass %;
a content of a raw material olefin having a double bond
position at a 4-positon is from 17 to 19 mass %;
a content of a raw material olefin having a double bond
position at a 5-positon is from 13 to 15 mass %; and
a content of a raw material olefin having a double bond
position at a 6-positon is from 11 to 13 mass %.

* * * * *